United States Patent [19]
Calenoff et al.

[11] Patent Number: 5,084,379
[45] Date of Patent: Jan. 28, 1992

[54] FLUOROMETRIC ASSAY OF CHYMOPAPAIN HYPERSENSITIVITY AND REAGENTS THEREFOR

[75] Inventors: Emanuel Calenoff, Burlingame; Ruth M. Jones, Redwood City; Yuh-Geng Tsay, San Jose; Myron A. Beigler, Los Altos Hills, all of Calif.

[73] Assignee: BioWhittaker, Inc., Walkersville, Md.

[21] Appl. No.: 529,784

[22] Filed: May 25, 1990

Related U.S. Application Data

[63] Continuation of Ser. No. 144,680, Jan. 14, 1988, abandoned, which is a continuation of Ser. No. 489,897, Apr. 29, 1983, abandoned.

[51] Int. Cl.$^5$ .................... C12Q 1/37; G01N 33/53
[52] U.S. Cl. ........................ 435/7.1; 435/7.4; 435/23; 435/24; 436/513
[58] Field of Search ............... 435/2, 21, 184, 177, 435/180, 299, 300, 301, 810; 436/513, 548, 531, 539

[56] References Cited

U.S. PATENT DOCUMENTS

| | | | |
|---|---|---|---|
| 3,941,876 | 3/1976 | Marinkovich | 436/513 |
| 3,997,404 | 12/1976 | Waters | 435/300 X |
| 4,002,532 | 1/1977 | Weltman et al. | 435/7 |
| 4,240,751 | 12/1980 | Linnecke et al. | 435/808 X |
| 4,256,833 | 3/1981 | Ali et al. | 436/513 X |
| 4,273,756 | 6/1981 | Ling et al. | 436/534 X |
| 4,298,592 | 11/1981 | Lin et al. | 435/7 X |
| 4,376,110 | 3/1983 | David et al. | 436/529 X |
| 4,444,879 | 4/1984 | Foster et al. | 436/513 X |
| 4,448,882 | 5/1984 | Brodbeck et al. | 435/28 X |
| 4,450,231 | 5/1984 | Ozkan | 436/539 |
| 4,454,226 | 6/1984 | Ali et al. | 436/513 X |
| 4,465,776 | 8/1984 | Cidlowski et al. | 435/7 X |
| 4,501,970 | 2/1985 | Nelson | 250/458.1 |
| 4,504,579 | 3/1985 | Sun | 435/188 X |

FOREIGN PATENT DOCUMENTS 0106662  4/1984  European Pat. Off.

OTHER PUBLICATIONS

Automated Immunoanalysis Part 2, Robert F. Ritchie (editor), New York, Marcel Dekker, Inc., 1978, pp. 336-342.

Kapsalis et al., "Correlation Between Hypersensitivity to Parental Chymopapain and the Presence of IgE Anti--Chymopapain Antibody", Clinical and Experimental Immunology, vol. 33, 1978, pp. 150-158.

Biological Abstracts, vol. 67(3) (1978), Abstract No. 13094, Kapsalis et al.

Enzyme Immunoassay, Maggio (ed.), CRC Press, Boca Raton, Florida, 1980, pp. 173-179.

Manual of Clinical Immunology, Rose et al. (ed.), American Society of Microbiology, Washington, D.C., 1976, pp. 596-602.

Hellsing, K. et al., Chapter 3, pp. 67-112, Automated Immunoanalysis (Marcel Dekker, New York) 1978.

Ceska, M. et al., Effect of Non-Ionic Polymers on Radioallergoimmunosorbent Reactions, Eur. J. Immunol., 2:58-62 (1972).

Shalev, A. et al., J. of Immunol. Methods, 38:125-139 (1980).

Hill, P. et al., J. Immunol. Meth. 45:51-63 (1981).

Eisenbrey, A. et al., J. Immunol. Meth., 58:365-373 (1983).

Primary Examiner—Sam Rosen
Attorney, Agent, or Firm—Banner, Birch, McKie & Beckett

[57] ABSTRACT

A method for identifying and quantifying chymopapain-specific IgE antibody levels in patient serum comprising binding chymopapain-specific IgE, if any, in the serum with chymopapain adhering to an insoluble support, conjugating the serum IgE with a labeled anti-IgE antibody, and measuring the level of labeled compound bound to the insoluble support or in the solution removed therefrom. Special reagents and their manufacture are also disclosed.

7 Claims, No Drawings

FLUOROMETRIC ASSAY OF CHYMOPAPAIN HYPERSENSITIVITY AND REAGENTS THEREFOR

This application is a continuation of Ser. No. 07,144,680 filed Jan. 14, 1988, which was a continuation of Ser. No. 06/489,897 filed Apr. 29, 1983, both now abandoned.

FIELD OF THE INVENTION

This invention relates to determining allergic hypersensitivity to chymopapain. More particularly, this invention relates to methods and reagents for determining the presence and relative concentrations of chymopapain-specific IgE antibodies in patient serum.

BACKGROUND OF THE INVENTION

The commercial distribution and injection of the proteolytic enzyme chymopapain for the non-surgical treatment of prolapsed intervertebral discs has recently obtained regulatory approval, and use of this method to replace traditional disc surgery is rapidly increasing. Many patients injected with chymopapain, however, have shown symptoms of anaphylactic hypersensitivity, ranging from mild urticaria to circulatory collapse and death. The injection of a high concentration of enzyme into the disc greatly accentuates the hypersensitivity reaction and can cause fatal reactions. Allergic hypersensitivity to chymopapain is now believed to be present in as much as one percent of the total population, perhaps because of frequent ingestion of chymopapain in foods such as papaya, pinapple, and particularly tropical fruit juices. Anaphylactic shock is therefor a major, serious risk associated with this new treatment.

DESCRIPTION OF THE PRIOR ART

Radiometric and fluorometric methods for identifying and measuring allergen-specific IgE levels in patient serum are commercially available and are known as the RAST test, for example. U.S. Pat. Nos. RE-29,474; 3,555,143; 3,648,346; 3,720,760 and 3,966,898 relate to these methods and reagents therefor. Enzymatic immunological methods for identifying and quantifying antigens and antibodies in liquids are widely used and are known as the ELISA and EIA tests, for example. Basic technologies for enzymatic assays and reagents therefor are disclosed in U.S. Pat. Nos. RE-29,169 and 3,839,153, for example.

A review of the current state of the art with regard to immunoassays for the detection of proteins in solutions is provided by R. Rose et al, *Manual of Clinical Immunology*, 2nd ed. American Society for Microbiology, Washington, pp 327-429, 775-849 (1980) and by A. Voller et al, *Immunoassays for the 80's*, University Park Press, Baltimore (1981), and the publications cited therein, the entire contents of both publications being hereby incorporated by reference. The chapter therein by T. A. E. Platts-Mills et al, "Radioimmunoassays in Allergy", pp 289-311, and the publications cited therein provide a comprehensive review of the field of this invention.

Procedures for binding proteins to insoluble supports have been primarily described. Covalent bonding of antibodies to insoluble supports has been described in U.S. Pat. Nos. 3,551,555, 3,553,310, 4,048,298 and RE-29,474. Binding of antibodies to polystyrene by adsorption has been described in U.S. Pat. Nos. 3,646,346 and 4,092,408, for example. Allergens have been covalently bonded to a variety of insoluble supports as described in U.S. Pat. No. 3,720,760.

Polyethylene glycol has been used in protein fractionation processes as described by A. Polson et al, *Biochim. Biophys Acta*, vol. 82, pp 463-475 (1964) and A. Polson et al, *Vox Sang*, vol. 23, pp. 107-118 (1972).

A solid phase radioimmunoassay, similar to the RAST, has been developed in an attempt to predict anaphylactic reactions in patients to be injected with chymopapain, and an evaluation of this test is described by A. Kapsalis et al, *Clin. Exp. Immunol.* 33, 150-158(1978). Data collected from sera of 1263 patients were reported. Of these, 12 patients had reacted to chymopapain injection. Seven (58.3 percent) of the 12 were found to test positive by the radioimmunoassay, using a criterion of 0.9 mg per 0.2 ml of serum. This low percentage was not a level of sensitivity giving confidence. Reducing the criterion for a positive result to 0.8 mg per 0.2 ml would increase the positive test to 67 percent but increase false positive results to 8.4 percent. One additional patient would have been officially excluded, but 49 additional patients would have been unnecessarily excluded because of false positive results. Because of the very serious risk associated with anaphylactic shock, the poorly sensitive RAST procedure does not meet the minimum requirements for practical use.

SUMMARY OF THE INVENTION

This invention relates to a method for identifying and determining the relative concentrations of chymopapain-specific IgE in serum samples. It comprises a first step of contacting an insoluble support having an allergenically active chymopapain adhered thereto with patient serum for sufficient time to permit binding of the chymopapain on the insoluble support with chymopapain-specific IgE antibody present in the serum. After binding, the serum is removed from the insoluble support.

The insoluble support is then contacted with a solution of labeled anti-IgE antibody for sufficient time to permit binding of the anti-IgE antibody with any IgE antibody bound to the chymopapain on the insoluble support. This solution is removed, and the amount of labeled anti-IgE antibody bound to the insoluble support or in the labeled anti-IgE antibody solution removed therefrom is measured.

When labeled anti-IgE antibody is conjugated with a fluorogenic enzyme, the amount of enzyme-labeled anti-IgE antibody bound to the insoluble support can be measured by contacting the insoluble support with a substrate which, in the presence of the fluorogenic enzyme, releases fluorescent compound. The amount of fluorescence in the solution is then measured. Preferably, the enzymatic activity of the chymopapain is reduced or blocked but without any significant reduction of allergenicity. The amount of chymopapain applied to the insoluble support preferably does not exceed 10 micrograms per $cm^2$ of surface area of insoluble support, and the anti-IgE antibody is a monoclonal antibody.

DETAILED DESCRIPTION OF THE INVENTION

The process of this invention comprises a first step of contacting an insoluble support having allergenic chymopapain adhering thereto with patient serum for a sufficient time to permit conjugation of the chymopapain with chymopapain-specific IgE antibodies in the patient serum, and then removing the patient serum from the support.

In this procedure the patient serum is preferably undiluted prior to contact with the supported allergen. The incubation time should be sufficient to permit substantial conjugation to occur, the time being temperature dependent. Suitable incubation times are from 30 to 180 minutes at temperatures within the range of from 18° to 40° C., the preferred contact time being from 60 to 120 minutes at temperatures within the range of from 20° to 26° C.

It is critical that the insoluble support have chymopapain adhered thereto which retains substantially all of its allergenic properties. The binding sites to which chymopapain-specific IgE antibody in patient serum would selectively bind must be essentially unaltered. Inhibition of enzymatic activity of chymopapain has been described by M. Ebata et al, *Biochem. Biophys. Res. Comm.* 9, 173(1962); M. Ebata et al, *Biochem. Biophys. Acta* 118, 201(1966); and A. White et al, *Principle of Biochemistry*, McGraw Hill: New York, p. 240 (1973).

Blocking agents suitable for eliminating or reducing enzymatic activity of chymopapain include the heavy metal cations of silver, mercury, arsenic, and lead, for example, p-mercuribenzoate and other mercurials, arsenicals, N-ethylmaleimide, and diisopropyl phosphofluoridate (DFP) and the like. Iodoacetic and bromoacetic acids, salts and esters thereof, and amides corresponding thereto are particularly useful. The choice of inhibitor and the specific conditions of treatment of the enzyme to effect complete enzymatic inhibition without altering the allergenic properties requires very critical conditions.

This reaction is carried out in suitable polar solvents, the preferred solvent being water, particularly an aqueous phosphate buffered saline solution. The iodoacetic acid to chymopapain molar ratio in solution is from 10 to 200 and preferably within the range of from 20 to 100. The reagent concentration in the reaction mixture is similarly critical, the chymopapain concentration being within the range of from 0.1 to 50 mg per ml and preferably within the range of from 0.5 to 5 mg per ml. The iodoacetic acid (compound) concentration in the reaction mixture is within the range of from 5 to 9 micrograms per ml and is preferably within the range of from 10 to 50 micrograms per ml.

For an optimum reaction, a number of other parameters are important in the reaction mixture. The pH should be within the range of from 4 to 9 and is preferably from within the range of 6 to 8. The reaction is advantageously carried out at a temperature of from 4° to 40° C. and preferably from 4° to 22° C. The reaction time is dependent upon the reaction temperature, the higher temperatures requiring shorter reaction times. For reactions within the range of from 4° to 22° C., reaction times of from one to 16 hours are preferred. The ultimate criterion however, is the desired reduction of enzymatic activity with retention of allergenic activity.

Following the reaction, purification of the chymopapain derivative is achieved by conventional purification procedures such as dialysis, gel filtration chromatography, ultrafiltration and ion exchange chromatography. Further details are described in our U.S. Pat. No. 4,499,065, which is hereby incorporated by reference.

The insoluble support having chymopapain adhering thereto is an important aspect of this invention. The diagnostic support preferably has a solid, water-insoluble surface. The surface can be widely varied.

The surface may take different forms, have different physical characteristics, can be of different chemical compositions, and may be of one or more compositions as a mixture of compositions, coatings or laminates or combinations thereof. The surface serves as a base or substrate which will retain a discrete existence in the assay solution so as to be discernable from the medium and usually separable from the medium. The surface serves to support chymopapain bound to it so that it is incapable of diffusing through the solution independent of the surface. In addition, the surface acts as a support for the compounds conjugated with the chymopapain bound to the surface. The surface is effectively nonfluid, discrete in that the surface is distinguishable from the liquid medium in which the surface is immersed, and provides a distinct base or foundation for supporting the compounds. The surface may exist in an electrostatically charged or uncharged form, being charged where such charges provide some advantage to the operation of a particular label system. The physical form of the support can embody any shape which is convenient for use including films, beads, containers, tubes, single and multiwelled plates and strips, and the like.

A wide variety of compounds can be employed as the solid support, the primary consideration being the binding of the chymopapain to the surface and the absence of interference with the reactions involved in the binding and use. A wide variety of organic and inorganic polymers, both natural and synthetic may be employed as the material for the solid support. Illustrative polymers include polyethylene, polypropylene, polybutylene, poly(4-methylbutylene), butyl rubber and other synthetic rubbers, silicone rubbers and silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be employed as the insoluble support may include silica gel, silicon wafers, glass, paper, insoluble protein, metals, metalloids, metal oxides, magnetic materials, semi-conductive materials, cermets or the like. In addition are included substances that form gels, such as lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as phospholipids, long chain (12–24 carbon atoms) alkyl ammonium salts and the like. Proteins such as gelatin can be used provided that the chymopapain is enzymatically inactive.

The surface will usually be polyfunctional or be capable of being polyfunctionalized so as to allow for covalent bonding between the reagents and the surface. Functional groups which may be present on the surface and used for linking can include carboxylic acids, aldehydes, amino groups, cyano groups, ethylenic groups, hydroxyl groups, or mercapto groups and the like. The manner of linking a wide variety of compounds to the various surfaces is well known and is amply illustrated in the literature, for example, "Immobilized Enzymes", Ichiro Chibata, Halsted Press, New York, 1978, and "Cuatrecasas", *J. Bio. Chem.* 245 3059(1970).

The lengths of the linking group may vary widely depending upon the nature of the compound being linked, the effect of the distance between the linked compound and the surface on the linked compound's properties, the potential for cross-linking of the linked compound, and the like. The linking group may be a bond or have up to about 12, usually not more than 10 atoms in a chain. The linking group may be aliphatic, alicyclic, aromatic, heterocyclic, or combinations thereof. The total number of atoms of the linking group will be not more than about 20, usually not more than about 16 atoms other than hydrogen, which will be carbon, oxygen as oxy or oxo, both oxo-carbonyl and non-oxo-carbonyl, nitrogen as amino or amido, or sulfur as thio or thiono. Illustrative groups include methylenecarbonyl, succinimidyl, alpha-haloacetyl, thiomethylene, glycyl or polyglycyl, succindioyl, maledioyl, glutardialkylidene, methylenephenyldiazo, and ureido.

A preferred diagnostic support of this invention comprises an opaque (preferably black) polystyrene or styrene-(vinyl monomer) copolymer having the chymopapain bound thereto by absorption, adsorption, ionic bonding, van der Waals adsorption, electrostatic bonding, or other non-covalent bonding., or covalent bonding. A particularly advantageous support for this procedure comprises a microwell plate or strip having a plurality of wells. The well surface or plastic cup inserts therein can constitute the chymopapain support. Most advantageously, the microwell plate or the well inserts are opaque to light so that excitation light applied to a well or fluorescense generated in response thereto does not reach or influence contents of the surrounding wells. With this system each well can be employed as a test system independent of the other wells.

For example, chymopapain can be applied by non-covalent bonding to a polystyrene microwell or polystyrene insert cup for a microwell by the following procedure. The concentration of chymopapain on the insoluble support is critical to sensitivity of the test, concentrations of from 0.01 to 10 micrograms per cm$^2$ being suitable and concentrations of from 0.05 to 0.5 micrograms per cm$^2$ being preferred.

The polystyrene surface is washed with a cleaning liquid such as methanol. The chymopapain in an aqueous buffer solution is placed in the well or insert cup, incubated for from 2 to 24 hours at from 18° to 40° C. and removed. The buffer solution characteristics are critical, phosphate buffer solutions (PBS) having a pH within the range of from 7 to 9.4 and from 7.5 to 8.5 being preferred. The chymopapain concentration in the solution is from 0.0005 to 0.5 mg per ml and preferably from 0.005 to 0.1 mg per ml. The well or insert cup is then dried, rinsed with an aqueous sucrose or sorbitol solution, and vacuum dried.

The enzyme activity of the chymopapain is preferably deactivated but with full retention of its allergenic properties. The process of reducing enzymatic activity must not change the spectrum of allergens in the chymopapain or the relative proportions of allergen (the allergenic profile). If these are altered, the utility of the product for accurately predicting and measuring allergenic hypersensitivity to injected chymopapain formulations, would be seriously impaired. In order to completely assess a risk of hypersensitive reaction, it is critical that hypersensitivity be measured with regard to all allergenic components, and a test which measures hypersensitivity to only one of several components present in the chymopapain would not correctly assess the patient risk.

In one procedure for coating a polyethylene or polystyrene surface with chymopapain, for example, the chymopapain is applied to the surface in a buffered solution containing an azide. A solution of enzyme having a concentration of from about 0.0005 to about 0.5 mg per ml of protein is prepared from the concentrated extract in from about 0.005 to about 0.01 molar sodium phosphate and from about 0.01 to about 0.1 weight percent sodium azide. The sodium phosphate buffers the solution to a pH of from about 7.1 to about 9.5. This solution is then coated on the polymer surface and incubated at room temperature for from 6 to 72 hours and preferably from 12 to 48 hours. These coated surfaces are then washed with from about 0.005 to about 0.1 molar sodium phosphate having a pH of 6.9 to 8.4 and containing from about 0.01 to about 0.1 weight percent sodium azide. A 0.1 molar solution of Tris-HCl and 0.02 weight percent sodium azide buffered at a pH of 8 is preferred for both the incubation and the washing medium.

Additional details for affixing protein to tubes or other apparatus is provided in the publication by C. M. Ling and L. R. Overby, "Prevalence of Hepatitis B. Antigen as Revealed by Direct Radioimmunoassay with $^{125}$I Antibody," *Journal of Immunology*, Vol. 109, No. 4, October 1972. Although the coating method has been described with reference to a coated tube, the coating method may be utilized to prepare coated inserts, beads, or any apparatus for use with wells, etc. by dipping the inserts in the enzyme solution and following the remaining procedure.

Alternatively, enzymatically inactive chymopapain can be covalently bonded to a water-soluble protein or protein-like polymer having an affinity for the insoluble substrate. The enzyme-polymer product is then adhered to the insoluble substrate by non-covalent bonding such as by adsorption or absorption. This procedure is described in commonly assigned, copending application Ser. No. 444,622 filed Nov. 26, 1982, the entire contents of which are hereby incorporated by reference.

Suitable water-soluble proteins include serum albumins of bovine (BSA), human (HSA), rabbit (RSA), goat (GSA), sheep (SSA), horse (HOSA), etc.; serum gamma Globulin of the previously described animals; and other animal proteins such as ovalbumin, fibrinogen, thrombin, transferrin, glycoproteins, etc. Suitable water-soluble amino acid polymers include polylysine, polyglutamic acid, polyalanine, polyhistidine, polymethionine, polyproline, etc. The enzyme can be covalently bonded to water-soluble protein or amino acid polymer with conventional coupling agents using methods which are known in the art.

Preferably the coupling agent is a carbodiimide such as 1-ethyl-3-(3-N,N-dimethylaminopropyl)carbodiimide hydrochloride and 1-cyclohexyl-3(2-morpholinoethyl) carbodiimide methyl-p-toluenesulfonate. Other suitable coupling agents include aldehyde coupling agents having either ethylenic unsaturation such as acrolein, methacrolin, or 2-butenal or having a plurality of aldehyde groups such as glutaraldehyde, propanedial or butanedial. Other coupling agents include bifunctional NHS-esters such as disuccinimidyl suberate, disuccinimidyl tartarate, bis-[2-(succinimidooxycarbonyloxy)ethyl]sulfone, disuccinimidyl (N,N'-diacetylhomocystine, dithiobis(succinimidyl propionate), ethylene glycolbis(succinimidyl succinate); heterobifunctional reagents such as N-5-azido-2-nitrobenzoyloxy succinimide, p-azidophenacyl bromide, p-azidophenylglyoxal, 4-fluoro-3-nitrophenyl azide, N-hydroxysuccinimidyl-4-azidobenzoate, m-maleimidobenzoyl N-hydroxysuccinimide ester, methyl-4-azidobenzoimidate HCl, p-nitrophenyl 2-diazo-3,3,3-trifluoropropionate, N-succinimidyl-6(4'-azido-2'-nitrophenylamino)hexanoate, succinimidyl 4-(N-maleimido-methyl)cyclohexane-1-carboxylate, succinimidyl 4-(p-maleimidophenyl)butyrate, N-succinimidyl (4-azidophenyldithio)-propionate, N-succinimidyl 3-(2-pyridyldithio)-propionate, N-(4-azidophenylthio)phthalimide, homobifunctional reagents such as 1,5-difluoro-2,4-dinitrobenzene, 4,4'-difluoro-3,3'-dinitrodiphenylsulfone, 4,4'-diisothiocyano-2,2'-disulfonic acid stilbene, p-phenylenediisothiocyanate, carbonylbis(L-methionine p-nitrophenyl ester), 4,4'-dithiobisphenylazide, erythritolbiscarbonate; and bifunctional imidoesters such as dimethyl adipimidate·2HCl, dimethyl suberimidate, dimethyl 3,3'-dithiobispropionimidate·2HCl, 2-iminothiolane·HCl. Covalent bonding of chymopapain to the insoluble protein can be carried out with the above reagents by conventional, well-known reactions, for example in the aqueous solutions at a neutral pH, at temperatures of less than 10° C. for 18 hours or overnight.

In an alternate procedure, the support surface can be first coated with an inert protein. This procedure is described with respect to polyethylene or polystyrene tubes but is equally suitable for wells, beads, etc. To the reactive bottom part, in accordance with this procedure, is attached an inert protein. The term "inert protein" means a protein which does not take part in the immunochemical reaction and does not adversely affect the biological substance. The proteins that can be used are well known to those skilled in the art. They include any proteinaceous material such as serum albumins or globulins obtained from various animal species or can be other uniform materials. Particularly preferred are bovine gamma globulin and gelatin since these are readily available. The proteinaceous material employed should be sufficiently homogeneous so that an essentially continuous surface can be obtained by the use thereof. Such a surface is readily obtainable with the above proteins. Enzymatically inactive chymopapain is then bonded to the inert proteins More specifically, the plastic surfaces are treated by a process which comprises (a) coating the surface by adsorption with an inert protein under adsorbing conditions (b) attaching enzyme extract to the inert protein coating, (c) treating the coupled part with a stabilizing agent to stabilize the enzyme extract against denaturization, and (d) drying the reactive part under drying conditions that will not substantially reduce the allergenic activity of the enzyme.

The amount of inert protein required to give optimum results is dependent on the nature of the inert protein and the surface This amount is readily determinable by those skilled in the art. Typically, only a thin film (e.g., at least a thickness of one layer of molecules) of protein is attached to the surface Generally, this is a sufficient amount to effect a uniform coating to which the biologically active substance may by attached. It is advantageous to make the charge distribution on the surface about equal to that of the inert protein to be applied. This is accomplished by washing the surface with an aqueous buffer solution having about the same pH as the coating solution containing the inert protein prior to coating.

The enzymatically inactive chymopapain can be attached by any suitable means. Such suitable means known to the art include adsorption, covalent binding, ionic binding and entrapment. Methods for covalently binding the enzyme to the inert protein are disclosed in U.S. Pat. Nos. 3,553,310 and 3,639,558, which are hereby incorporated by reference. A preferred method of covalent binding to inert protein comprises first treating the protein with an aldehyde coupling agent, followed by application of the enzyme under conditions which permit the aldehyde to covalently bind to both the inert protein and the enzyme. Suitable aldehyde coupling agents are those which have either ethylenic unsaturation or a plurality of aldehyde groups, or both, such as acrolein, methacrolein and 2-butenal. Dialdehydes can be employed such as glutaraldehyde, propanedial and butanedial.

When one of these aldehydes is contacted with the surface of the inert protein, the protein is stabilized and polymerized by cross-linking, and aldehyde active moieties are fixed to the surfaces. These moieties are believed to be carbonyl groups and are highly reactive to the amine groups of the enzyme since they form covalent bonds between the protein particles and the enzymes.

The aldehyde or ethylenically unsaturated coupling procedures can also be used to covalently bond the enzyme to other surfaces having primary amino groups For example, polylysine coated polystyrene can be coupled to enzyme with glutaraldehyde Alternative to aldehydes, there may be used other coupling moieties such as compounds having two or more of the following reactive groups azo, sulfonic acid or fluoro groups activated by nitro groups, azide, imine or reactive chloro groups connected to a ring having appropriate resonance structure. These reactive groups are capable of reacting with the primary amino, sulfylhydryl, carboxylic, hydroxyl and phenolic groups in the substances constituting the inert protein as well as the enzyme to be coupled thereto A representative list of such coupling agents is bisdiazobenzadine, disulfonic acid, tetraazo-p-phenylenediamine difluorodinitrobenzene, difluorodinitrophenylsulfone, carbodiimides, toluene diisocyanate, cyanuric chloride, dichlorotriazine, N-t-butyl-5-methylisoxazolium perchlorate. Carbodiimides which can be employed are N,N-dicyclohexylcarbodiimide, 1-ethyl-3(3-dimethylaminopropyl)carbodiimide hydrochloride, and 1-cyclohexyl-3(2-morpholinyl(4)-ethylcarbodiimide)methyl-p-toluene sulfonate.

Alternatively chymopapain can be attached by adsorption according to the procedure described in U.S. Pat. No. 3,551,555. The solid support surface can also be coated with a material which will bind to the enzyme through an isocyanate bond such as that provided by polyether isocyanate coatings (HYPOL-2000, W.R. Grace & Co., Lexington, Mass.).

Procedures for binding reagents to glass surfaces are known in the art and are described in U.S. Pat. No. 4,280,992, for example. Methods used of binding the enzyme to the glass are not critical Frosted glass is preferred. Enzymatically inactivated chymopapain can be bound to the glass surface by physical or chemical methods. The latter are preferred when firm and permanent binding of a large amount of enzyme to the glass is desired.

Binding by a physical method can be attained mainly by physical adsorption (van der Waals adsorption). Thus, the glass may be dipped in a solution of the inactivated enzyme and incubated, or allowed to stand, for an appropriate period of time to form physical binding The solution can have a concentration of generally 0.01 to 400 g per liter and preferably 0.1 to 1.0 g per liter. The dipping or immersion treatment can be carried out, for example, at a temperature of 0° to 45° C. for one to 48 hours.

As a suitable chemical method, the inactivated enzyme can be bound to glass surfaces, and preferably frosted glass surfaces, with the aid of a silane coupling agent, and if necessary, a cross-linking agent. There may be used any silane coupling agent having in its molecule both a functional group reactive with the glass and a functional group reactive with the enzyme and/or the cross-linking agent. Examples of suitable functional groups reactive with the glass include those reactive with a silanol group of the glass, and include, for example, alkoxysilyl groups (such as methoxy or ethoxy-substituted silyl groups), and the like. Examples of suitable functional groups reactive with the enzyme and/or the cross-linking agent are those reactive with amino, carboxyl and/or thiol group(s), and include, for instance, carboxyl, epoxy, haloalkyl (such as chloroethyl and chloropropyl), aldehyde, primary and secondary amino, thiol, isocyanate, carboxylate, imino and nitrile (or cyano) groups, and the like. More specifically, examples of suitable functional groups reactive with the amino group are carboxyl, epoxy, haloalkyl and aldehyde groups. Suitable functional groups reactive with the carboxyl group include, for example, primary and secondary amino, and epoxy groups. Suitable functional groups reactive with the thiol group include thiol, epoxy, haloalkyl and aldehyde groups, and the like.

In binding the chymopapain to the glass, the silane coupling agent may be used with or without the cross-linking agent. The cross-linking agent may be selected according to the kind of the silane coupling agent. There may be used any cross-linking agent which can cross-link the silane coupling agent with the enzyme. As such cross-linking agent there may be mentioned, those compounds that can cross-link the amino, carboxyl or thiol group of the silane coupling agent with the amino, carboxyl or thiol group of the immunologically active substance, such as those capable of producing a cross-linkage between the thiol group and the thiol group, or between the amino group and the thiol group. Examples of suitable compounds which can cross-link between the amino group and the amino group are aliphatic dialdehydes (such as glyoxal, malonaldehyde, succinaldehyde, glutaraldehyde) and dichlorotriazines (such as 2-amino-4,6-dichloro-s-triazine), and the like. Suitable cross-linking agents between the thiol group and the thiol group are, for instance, dimaleimide compounds (such as N,N'-o-phenylenedimaleimide, N,N'-m-phenylenedimaleimide). Suitable cross-linking agents between the amino group and the thiol group are exemplified by maleimidocarboxyl-N-hydroxysuccinimide esters (such as m-maleimidobenzoyl-N-hydroxysuccinimide ester, and 4-(maleimidomethyl)cyclohexane-1-carboxyl-N-hydroxysuccinimide ester).

Adsorbents useful in the process of the invention as solid supports for chymopapain are known in the art. Suitable materials are listed below:

ADSORBENTS AND ABSORBENTS

Non-ionic cellulose
  e.g , Whatman (Clifton, New Jersey, U.S.A.) types—
  CF-1 ®, long fiber powder
  CF-11 ®, medium fiber powder
  CC-31 ®, microgranular powder
  CC-41 ®, microgranular powder
  e.g., Bio-Rad (Richmond, Calif., U.S.A.) types—
  Cellex ®N-1, powder
  Cellex ®410, powder
Silica gel
  e.g., Whatman type—SG 81, loaded paper; or Bio-Rad types—Bio-Sil ® A or Bio-Sil ® HA
Hydroxylapatite (Bio-Rad)
Alumina; acid, base, or neutral types (Bio-Rad)
Alumina C-gamma gel (Bio-Rad)
Calcium phosphate
Hydroxypropyl dextran
  e.g., Pharmacia (Piscataway, N.J., U.S.A.) type—Sephadex ® LH 20
Dextran (Pharmacia)
Dextran sulfate (Pharmacia)
Alkyl agaroses
  e.g., Pharmacia types—octyl-Sepharose ® Cl-4B or phenyl-Sepharose ® Cl-4B
  e.g., Miles Research Products (Elkhart, Ind., U.S.A.) types—omega-amino alkyl agaroses
Lectin-agarose (Miles Research Products)
Poly-L-lysine agarose (Miles Research Products)
Plastics, e.g., polystyrene, polyethylene, and polypropylene

ANION EXCHANGE MATERIALS

Diethylaminoethyl (CEAE) cellulose
  e.g., Whatman types—
  DE-1 ®, floc
  DE-11 ®, powder
  DE-22 ®, fibrous
  DE-23 ®, fibrous
  DE-32 ®, dry, microgranular
  DE-52 ®, wet, microgranular
  DE-81 ®, paper
  e.g., Bio-Rad type—Cellex ® D, fibrous
Diethylaminoethyl (DEAE) agarose
  e.g., Bio-Rad type—DEAE Biogel ® A
Diethylaminoethyl (DEAE) dextran
  e.g., Pharmacia type—DEAE Sephadex ®, bead
Aminohexyl-Sepharose ® 4B (Pharmacia)
Ecteola cellulose
  ET-11 ®, powder
  ET-41 ®, powder (high purity)
  ET-81 ®, paper
  e.g., Bio-Rad type—Cellex ® E, fibrous
Triethylaminoethyl (TEAE) cellulose
  e.g., Bio-Rad type—Cellex ® T, fibrous
Diethyl-(2-hydroxypropyl)-amino (QAE) cellulose
  e.g., Bio-Rad type - Cellex ® QAE, fibrous
Diethyl-(2-hydroxypropyl)-amino (QAE) dextran
  e.g., Pharmacia type—QAE-Sephadex ®
Benzolyated diethylaminoethyl cellulose
  e.g., Bio-Rad type—Cellex ® BD, fibrous

CATION EXCHANGE MATERIALS

Cellulose phosphate
  e.g., Whatman types—
  P-1 ®, floc
  P-11 ®, powder

P-41 ®, powder (high purity)
P-81 ®, paper
Carboxymethyl cellulose
   e.g., Whatman types—
CM-1 ®, floc
CM-11 ®, powder
CM-22 ®, fibrous
CM-23 ®, fibrous
CM-32 ®, dry, microgranular
CM-52 ®, wet, microgranular
CM82 ®, paper
   e.g., Bio-Rad type—Cellex ® CM, fibrous
Carboxymethyl dextran
   e.g., Pharmacia type—CM-Sephadex ®
Phosphoryl cellulose
   e.g., Bio-Rad type—Cellex ® P, fibrous
Carboxymethyl agarose
   e.g., Bio-Rad type—CM Biogel ® A
   e.g., Pharmacia type—CH-Sepharose ® 4B
Sulphopropyl dextran
   e.g, Pharmacia type—SP-Sephadex ®

Reagents formed by chemically coupling or combining the chymopapain to polymeric carrier particles of varying particle size are well-known, e.g., U.S. Pat. Nos. 3,882,225; 3,957,931; 3,825,525; 3,629,558; 3,565,987; 3,553,310; 3,407,076; 3,236,732; 3,096,250; 4,092,114; 4,140,662; 4,210,723; 4,226,747; 4,259,313; 3,088,875; 3,766,013; 3,619,371; 3,809,613; 3,853,987; 3,963,441; 3,551,555; and 3,649,346. Netherlands Patent No. 7,201,308; and British Patent No. 1,257,263.

When covalent bonding of the chymopapain to the polymer bead is desired, it is preferred to use for the bead a monomer which, after bead formation, retains a group which can react with amino, amido, or sulfonamido groups on the enzyme to be bound to the bead, e.g. chlorobenzyl, chloroacetyl, chloroethylcarbonyl, chloroethylsulfonyl, acryloyl, or vinyl-sulfonyl group.

Also the surface groups can be bonded to enzyme through bifunctional-linking groups reacted with the reactive bead surface group and with the chymopapain.

The beads are usually prepared by polymerizing one or more vinyl monomers by standard procedures. Suitable vinyl monomers which can be polymerized and/or copolymerized with each other in any proportions and/or with other monomers to yield the desired beads include monovinylidene carboxyclic monomers, e.g., styrene, alpha-methylstyrene, ar-(t-butyl)styrene, ar-methylstyrene, ar,ar-dimethylstyrene, ar-chlorostyrene, ar-(t-amyl) styrene, ar-bromostyrene, ar-fluorostyrene, ar-cyanostyrene, ar-methoxystyrene, ar-ethylstyrene, ar-hydroxymethylstyrene, ar-ethoxystyrene, ar-chloro-ar-methylstyrene, ar,ar-dichlorostyrene, ar,ar-difluorostyrene, vinyl naphthalene, and other such emulsion polymerizable monomers having not more than 26 carbon atoms; esters of alpha, betaethylenically unsaturated carboxylic acids which polymerize to form non-film forming polymers, e.g., methyl methacrylate, chloroethyl methacrylate, n-butyl methacrylate, ethyl methacrylate, isobutyl methacrylate, isopropyl methacrylate, phenyl methacrylate, butyl chloroacrylate, cyclohexyl chloroacrylate, ethyl chloroacrylate, methyl chloroacrylate, isopropyl chloroacrylate and other such esters capable of being polymerized to form hard polymers; alpha, betaethylenically unsaturated esters of non-polymerizable carboxylic acids, e.g., vinyl benzoate, vinyl toluate ar-ethylbenzoate, allyl ar-ethylbenzoate, vinyl trimethyl-group which can react with amino, amido, or sulfonamido groups on the enzyme to be bound to the bead, e.g. chlorobenzyl, chloroacetyl, chloroethylcarbonyl, chloroethylsulfonyl, acryloyl, or vinyl-sulfonyl group.

Also the surface groups can be bonded to enzyme through bifunctional-linking groups reacted with the reactive bead surface group and with the chymopapain.

The beads are usually prepared by polymerizing one or more vinyl monomers by standard procedures. Suitable vinyl monomers which can be polymerized and/or copolymerized with each other in any proportions and/or with other monomers to yield the desired beads include monovinylidene carboxyclic monomers, e.g., styrene, alpha-methylstyrene, ar-(t-butyl)styrene, ar-methylstyrene, ar,ar-dimethylstyrene, ar-chlorostyrene, ar-(t-amyl) styrene, ar-bromostyrene, ar-fluorostyrene, ar-cyanostyrene, ar-methoxystyrene, ar-ethylstyrene, ar-hydroxymethylstyrene, ar-ethoxystyrene, ar-chloro-ar-methylstyrene, ar,ar-dichlorostyrene, ar,ar-difluorostyrene, vinyl naphthalene, and other such emulsion polymerizable monomers having not more than 26 carbon atoms; esters of alpha, beta-ethylenically unsaturated carboxylic acids which polymerize to form non-film forming polymers, e.g., methyl methacrylate, chloroethyl methacrylate, n-butyl methacrylate, ethyl methacrylate, isobutyl methacrylate, isopropyl methacrylate, phenyl methacrylate, butyl chloroacrylate, cyclohexyl chloroacrylate, ethyl chloroacrylate, methyl chloroacrylate, isopropyl chloroacrylate and other such esters capable of being polymerized to form hard polymers; alpha, beta-ethylenically unsaturated esters of non-polymerizable carboxylic acids, e.g., vinyl benzoate, vinyl toluate ar-ethylbenzoate, allyl ar-ethylbenzoate, vinyl trimethylacetate, vinyl pivalate, vinyl trichloroacetate and other such monomers wherein the unsaturated moiety has from 2 to 14 carbon atoms and the acid moiety has from 2 to 12 carbon atoms; alpha, beta-ethylenially unsaturated nitriles, e.g., such as nitriles having not more than 12 carbon atoms; other polymerizable vinyl monomers such as vinyl chloride, vinyl bromide and the like.

After conjugation of chymopapain-specific IgE antibody with the chymopapain adhering to the insoluble support has occurred, the solution is removed therefrom. Surplus liquid is removed and the solid surface is then rinsed with a suitable rinse solution such as a phosphate buffer solution (PBS) having a pH of from 6 to 8.5.

The second step of the process of this invention comprises contacting the insoluble support with a labeled anti-IgE antibody. The incubation is continued for sufficient time to permit serum IgE conjugated with chymopapain (if any) on the insoluble support to conjugate with the anti-IgE antibody. After incubation, the excess liquid is removed, and the surface of the insoluble support is rinsed with a weak solution as described above with respect to the first step to remove unconjugated antibody.

Anti-IgE antibodies are available from many sources, and the methodology for producing them is well known and is described in several of the patents and publications cited above. The preferred antibodies are monoclonal antibodies. The technology for making monoclonal antibodies is well developed, and the procedures suitable for making monoclonal anti-IgE antibodies are described by D. Catty, et al in "Antisera in Immunoassays with special Reference to Monoclonal Antibodies to Human Immunoglobulins", Immunoassay's for the 80's, supra, pp 133-153 and the publications cited therein, the entire contents of which are hereby incorporated by reference.

The anti-IgE antibody can be labeled with a variety of moieties. Suitable labeling moieties are radioactive labels, enzyme labels, chemiluminescent labels, fluorescent labels, metals and metal oxides, electron-spin labels, etc. The sensitivity with which a labeling moiety can be measured depends upon the nature of the signal it generates, the ability to detect that signal, and upon the intensity of the signal available per unit amount of marker molecule, that is, its specific activity.

With radioactive labels, the signal is decay radiation. Because of the penetrating properties of the emissions generated, radioactive decay can be detected easily. Modern counting equipment very efficiently measures the radioactivity. Also, there is a range of specific activities offered by isotopes currently used for tagging.

The specific activity of the radioactively tagged compound depends upon several factors: the half-life of the isotope used for labeling, the isotopic purity of the label and how much of the label has been incorporated into the compound. Radioactive isotopes of many elements are available for tagging antibody reagents. Each isotope has its own unique half-life. Thus a wide variety of specific activities for tagging are available merely by selecting an optimum radioisotope. Table A lists several commonly used isotopes, their specific activities and half-lives. In general for use in the immunoassays, the higher the specific activity of the radio-labeled compound, the better.

TABLE A

PROPERTIES OF RADIOACTIVE ISOTOPES

| Isotope | Specific Activity of Pure Isotope (Curies/Mole) | Half-Life |
|---|---|---|
| $^{14}C$ | $6.25 \times 10^1$ | 5720 years |
| $^{3}H$ | $2.91 \times 10^4$ | 12.5 years |
| $^{35}S$ | $1.5 \times 10^6$ | 87 days |
| $^{125}I$ | $2.18 \times 10^6$ | 60 days |
| $^{32}P$ | $3.16 \times 10^6$ | 14.3 days |
| $^{131}I$ | $1.62 \times 10^7$ | 8.1 days |

The procedures available for labeling organic compounds with the radioactive isotopes listed in Table A are generally known in the art. Tritium labeling procedures are described in U.S. Pat. No. 4,302,438, for example. Labeling with radioactive iodine can be effected directly by the method described by Hunter et al in *Nature* 194, 4956 (1962) employing chloramine-T.

A wide variety of enzymatic labeling agents can be used. Examples of suitable systems, coupling procedures and substrate reactions therewith are disclosed in U.S. Pat. Nos 4,214,048, 4,312,943, and 4,302,438, for example, the entire contents of which are hereby incorporated by reference.

Fluorogenic enzymes (enzymes in the presence of which a substrate will produce a fluorescent product) are preferred labeling moieties. Methods for bonding enzymes to antibodies without impairing the ability of the antibody to selectively conjugate with antigen are well known in the art. Suitable enzymes and procedures for coupling them to antibodies are described in U.S. Pat. No. 4,190,496, for example, the contents thereof being hereby incorporated by reference. The preferred fluorogenic enzymes and the suitable substrates corresponding thereto include horse-radish peroxidase for which a suitable substrate is homovanillic acid or 4-hydroxy-3-methoxyphenylacetic acid, beta-galactosidase for which a suitable substrate is 4-methylumbelliferyl-beta-D-Galactoside, alkaline phosphatase for which a suitable substrate is 4-methylumbelliferyl phosphate and other umbelliferyl phosphates such as 4-carboxyumbellifery phosphate, and umbelliferyl phosphate 4-carboxy alkylesters, etc.

Examples of suitable procedures for enzyme labeling the anti-IgE antibody include the use of carbodiimides, dialdehydes, and bifunctional coupling reagents as described above for covalently bonding enzymatically inactivated chymopapain to water-soluble proteins such as BSA, for example.

Fluorescent labeled anti-IgE antibodies can be prepared from standard fluorescent moieties known in the art. Since antibodies and other proteins absorb light of wavelengths up to about 310 nm, the fluorescent moiety will have substantial absorption higher than 310 nm, normally higher than 350 nm, and preferably higher than about 400 nm. A number of different fluorescers are described by Stryer, *Science*, 162, 526 (1968) and L. Brand et al, "Fluorescent Probes for Structure," *Annual Review of Biochemistry*, 41, 843–868 (1972).

One group of fluorescers having a number of the desirable properties described previously are the xanthene dyes, which include the fluoresceins derived from 3,6-dihydroxy-9-phenyl-xanthhydrol and resamines and rhodamines, derived from 3,6-diamino-9-phenylxanthydrol. The rhodamines and fluoresceins have a 9-o-carboxyphenyl group, and are derivatives of 9-o-carboxyphenylxanthhydrol. These compounds are commercially available with substituents on the phenyl group which can be used as the site for bonding or as the bonding functionality. For example, amino and isothiocyanate substituted fluorescein compounds are available.

Another group of fluorescent compounds are the naphthylamines, having an amino group in the alpha or beta position, usually alpha position. Included among the naphthylamino compounds are 1-dimethylaminonaphthyl-5-sulfonate, 1-anilino-8-naphthalene sulfonate and 2-p-toluidinyl-6-daphthalene sulfonate. Other dyes include 3-phenyl-7-isocyanatocoumarin, acridines, such as 9-isothiocyanatoacridine and acridine orange; N-[p-(2-benzoxazolyl)phenyl]maleimide; benzoxadiozoles, such as 4-chloro-7-nitrobenzo-2-oxa-1,3-diazole and 7-(p-methoxybenzylamino)-4-nitrobenzo-2-oxa-1,3-diazole; strilbenes, such as 4-dimethylamino-4'-isothiocyanatostilbene and 4-dimethylamino-4'maleimidostilbene; N,N'dioctadecycloxa-carboxyanine p-toluenesulfonate; pyrenes, such as 8-hydroxy-1,3,6-pyrenetrisulfonic acid, and 1-pyrenebutyric acid, merocyanine 540, rose bengal, 2,4-diphenyl-3(2H)-furanone, as well as other readily available fluorescing molecules. These dyes, either have active functionalities or such functionalities may be readily introduced.

The linking group will normally have not more than about 10 atoms in the chain between the antibody and the chromophore, more usually having either a bond or from about 1 to 6 atoms in the chain. Antibodies have a number of active amino groups which can be used for covalently conjugating the chromophore to the antibody. Conveniently, the chromophore can have a nonoxocarbonyl functionality (including the nitrogen and sulfur analogs thereof) or active alpha-halocarbonyl functionality. Illustrative functionalities for linking the chromophore to the antibody include acyl halides, mixed anhydrides, imidate alkyl esters, isothiocyanate, chlorobromoacetyl or iodoacetyl, and the like.

Examples of compounds that react to form suitable fluorescent moieties of this type are the sulfhydryl reactive compounds, such as 5-iodoacetamidofluorescein and pyrenemaleimide; amino reactive compounds, such as fluorescein isothiocyanate, tetramethylrhodamine isothiocyanate, 2-methoxy-2,4-diphenyl-3-furanone, and eosin isothiocyanate (forms a phosphorescent product); hydroxyl reactive compounds such as anthroyl, trifluoroacetyl mixed anhydride; and carboxyl reactive compounds such as 4-bromo-methyl-7-methoxycoumarin.

The conditions for conjugation employ moderate temperatures 0° to 40° C. in aqueous media at moderate pH. Conjugation of chromophores to protein is known in the art. The, et al, *Immunology*, 18, 865 (1970); Cebra, et al, *J. Immunology*, 95-230 (1965); Goldman, *Fluorescent Antibody Methods*, Acedemic Press, New York (1968).

Anti-IgE antibodies labeled for chemiluminescer and chemiluminescer-quencher systems can be prepared from standard label moieties by methods known in the art as described, for example, in U.S. Pat. Nos. 4,104,029; 4,220,450; and 4,238,195.

The labeled anti-IgE antibody is applied to the insoluble support in an aqueous solution. The solution preferably contains suitable salts and buffers to preserve the reactants and facilitate the conjugation reaction. The solution preferably is a phosphate buffer solution (PBS), containing a water-soluble protein and a mild surfactant such as a polyoxyethylene sorbitan ester. The rinse solutions described herein can also be used.

A critical ingredient in the labeled anti-IgE antibody solution is the water-soluble protein. The preferred proteins are animal proteins, and the most preferred in order of preference are fetal bovine serum, gelatin and bovine serum albumin.

A preferred solution of this invention comprises from 0.1 to 5 micrograms per ml and preferably from 1 to 2 micrograms per ml anti-IgE antibody in an aqueous phosphate buffered solution having a phosphate molarity of from 0.00005 to 0.1 and preferably from 0.0001 to 0.05 and a pH of from 6.0 to 8.0 and preferably 7.2 to 7.6. The water-soluble protein concentration is from 0.1 to 10 weight percent and is preferably from 1 to 5 weight percent. A critical ingredient in the anti-IgE solution is polyethylene glycol having molecular weights of from 1000 to 8000 and preferably from 2000 to 4000 in concentrations of from 1 to 8 weight percent and preferably from 2 to 6 weight percent. Polyethylene glycols greatly increase the speed and sensitivity of the reaction. Another important ingredient is a non-ionic surfactant in concentrations of from 0.001 to 0.5 and preferably from 0.02 to 0.1 weight percent. Suitable non-ionic surfactants include those described above with respect to rinse solutions, for example. A preferred non-ionic surfactant is TRITON X-405. The surfactant surprisingly reduces the non-specific background fluorescence signal in the assay.

With the preferred anti-IgE solutions of this invention, the incubation time of the solutions with the insoluble support is temperature dependent. At temperatures of 18° to 40° C., incubation times of at least from 30 to 180 minutes can be used. The preferred temperatures are within the range of from 20° to 26° C., and at these temperatures, incubation times from 60 to 120 minutes can be employed. It should be appreciated that prolonged incubation times in any of the steps of this invention can reduce the efficacy of the process. Since rapid analysis is an objective of this invention, the lowest times which still yield the desired accuracy are preferred.

The solid support is then rinsed to remove residual, unconjugated labeled anti-IgE antibody. The rinse solutions described above are suitable.

The third step in the process of this invention is the measurement of the amount of labeled anti-IgE antibody bound to the insoluble support or in the solution removed therefrom.

In the preferred embodiment of this invention, the anti-IgE antibody is labeled with a fluorgenic enzyme, and the remaining steps will be described in conjunction therewith. In such event, the third step of the process of this invention comprises contacting the solid support with a solution of a substrate which undergoes chemical reaction in the presence of the fluorogenic enzyme for a time sufficient for fluorescent compounds to be formed. Suitable substrates and the enzymes they are converted by are known in the art and are described in U.S. Pat. No. 4,190,496, for example. Examples of substrates have been described hereinabove with respect to the corresponding fluorogenic enzyme.

The solid is contacted with an aqueous solution of the substrate containing from $10^{-2}$ to $10^{-10}$ molar and preferably from $10^{-4}$ to $10^{-5}$ molar concentrations of the substrate. Preferred additional reagents and buffers in the substrate solution include 2-amino-2-methyl-1-propanol buffer and magnesium chloride, for example.

The substrate solution is incubated with the insoluble support for sufficient time for the fluorescent reaction product to form. At temperatures of from 18° to 40° C., incubation times of from 5 to 240 minutes can be used. Preferably, the temperature is within the range of from 20° to 26° C., and the incubation time is from 30 to 90 minutes.

The fluorescence level in the solution is then measured. The equipment and procedures for determining the level of fluorescence in the substrate solutions are those conventionally employed in the art. The level of fluorescence is a function of the enzyme concentration on the insoluble support which is, in turn, a function of the amount of chymopapain-specific IgE antibody in the patient serum. By comparing the fluorescence levels with the levels measured by carrying out the procedure with control solutions containing known concentrations of the respective chymopapain-specific IgE antibody. The presence and precise concentrations of the corresponding chymopapain specific IgE antibody is determined. Suitable fluorometers are the fluorometers by Perkin-Elmer, American Instrument Company, and Turner Designs. The ALLERGENETICS ™ Fluorometer (Allergenetics, Inc., Mountain View, Calif.) is preferred.

Current therepeutic technology provides the doctor with several choices of treatment for patients having herniated discs. The most common approach used prior to development of enzymatic techniques for reducing herniated discs involved surgery. The risk of surgical damage to the spinal column was high, and the surgery was frequently unsuccessful in reducing the patient's pain. Enzymatic treatment with chymopapain is superior for treating herniated discs. Having confirmed the herniated condition with a standard myelogram, the doctor must determine if the patient has allergenic hypersensitivity to the therapeutic chymopapain compositions. Chymopapain allergy is thought to be derived from ingestion of foods containing chymopapain. Papaya and pinapple, fruit juices derived therefrom and tenderized meat are most suspected foods. Toothpaste, cosmetics and digestive acids are also thought to be sources of the allergy. Because one or more of these sources are part of most diets, all candidates for this treatment must be examined for allergic hypersensitivity. The method of this invention can be used to detect and measure sensitivity by determining chymopapain-specific IgE levels in patient serum with a far greater degree of accuracy and reliability than previously known procedures.

This invention is further illustrated by the following specific but non-limiting examples. Unless otherwise specified, temperatures are given in degrees Centigrade and concentrations are given as weight percents.

EXAMPLE 1

To 1.0 ml of an aqueous 0.1 N phosphate buffer solution having a pH of 6 and containing 0.1 wt.% chymopapain is added 0.01 ml of a 0.1 N phosphate buffer solution having a pH of 6 and containing 7.0 wt.% percent iodoacetic acid, both solutions being maintained at a temperature of 4°. After standing overnight at 4°, the mixture is dialyzed against 0.1 N phosphate buffer solution having pH's graduated from 6 up to 8.0.

EXAMPLE 2

The solution obtained from Example 1 is diluted 1:100 with 0.1 N phosphate buffer solution, pH 8.0, to a final concentration of 0.01 mg/ml chymopapain (0.001 wt.%). To each well is added 200 microliters of solution. It is allowed to stand overnight (16 hours), and the solution is removed, yielding a chymopapain coated microwell.

EXAMPLE 3

A well prepared according to Example 2 is washed three times with 0.1 N phosphate buffer solution, pH 8.0, and 100 microliters of serum is added to the well. After 2 hrs the serum is removed, and the well is washed three times with the phosphate buffer solution.

The microwell is then contacted with 100 microliters of a solution of alkaline phosphatase conjugated anti-human IgE monoclonal antibody prepared according to a modified procedure of M. O'Sullivan, et al, *Analytical Biochem.*, vol. 100, page 100 (1979). The monoclonal antibody is applied in a solution of 0.01 M phosphate buffered saline, pH 7.2, containing 4 wt.% polyethylene glycol having a molecular weight of 4000 (PEG 4000), 0.05 wt.% TRITON X-405, 2.5 wt. % fetal bovine serum (FBS) and 0.1 wt.% sodium azide preservative. The alkaline phosphatase conjugated anti-human IgE monoclonal antibody solution is removed from the microwell, and it is rinsed three times with the buffered rinse solution described above.

To the microwell is then added 100 microliters of a substrate solution containing $10^{-4}$ M 4-methyl umbelliferyl phosphate in 1.25 M 2-amino-2-methyl-propanol, pH 9.5, in deionized water containing 0.125 mM magnesium chloride and 0.1 wt.% sodium azide. After 60 minutes, the fluorescence level is read with a fluorometer with the excitation at 365 nm and the reading at 450 nm. By comparing the reading with levels measured by repeating the procedure with control solutions having known concentrations of chymopapain-specific IgE, the serum chymopapain specific IgE level in the patient serum is determined.

The invention claimed is:

1. A method for determining chymopapain hypersensitivity by determining chymopapain specific IgE antibody in a serum sample comprising the sequential steps of:
    a) contacting an insoluble support having allergenically active chymopapain adhered thereto with the serum sample for sufficient time to permit binding of chymopapain with chymopapain-specific IgE antibody and removing the serum from the insoluble support;
    b) contacting the insoluble support with a solution of anti-IgE antibody labeled with a fluorogenic enzyme for a time between 30 to 180 minutes and which is sufficient to permit binding of anti-IgE antibody with any IgE antibody bound to the insoluble support and removing the solution from the insoluble support;
    c) contacting the insoluble support with a solution of a substrate which in the presence of the fluorogenic enzyme undergoes chemical reaction to form a fluorescent compound for a time between 5 and 240 minutes;
    d) measuring the fluorescence level in the solution; and
    e) determining the amount of any labeled anti-IgE antibody bound to the insoluble support by comparing the fluorescence level of the solution with those of control solutions;
    wherein the insoluble support is a microwell that is opaque to light and wherein the chymopapain adhered to the microwell has the enzymatic sites thereof inactivated with full retention of its allergenic properties.

2. The method for determining chymopapain hypersensitivity of claim 1 wherein the chymopapain has the enzymatic sites thereof inactivated with an iodoacetic acid, a salt thereof, an ester thereof derived from an alcohol having from 1 to 6 carbons, or an amide thereof.

3. A method for determining chymopapain hypersensitivity by determining chymopapain specific IgE antibody in a serum sample comprising the sequential steps of:
    a) contacting an insoluble support having allergenically active chymopapain adhered thereto with the serum sample for sufficient time to permit binding of chymopapain with chymopapain-specific IgE antibody and removing the serum from the insoluble support;
    b) contacting the insoluble support with a solution of anti-IgE antibody labeled with a fluorogenic enzyme for a time between 30 and 180 minutes and which is sufficient to permit binding of anti-IgE antibody with any IgE antibody bound to the insoluble support and removing the solution from the insoluble support;
    c) contacting the insoluble support with a solution of a substrate which in the presence of the fluorogenic enzyme undergoes chemical reaction to form a fluorescent compound for a time between 5 and 240 minutes;
    d) measuring the fluorescence level in the solution; and
    e) determining the amount of any labeled anti-IgE antibody bound to the insoluble support by comparing the fluorescence level of the solution with those of control solutions;
    wherein the insoluble support is a microwell and the chymopapain has the enzymatic sites thereof inactivated with full retention of its allergenic properties.

4. The method for determining chymopapain hypersensitivity of claim 3 wherein the chymopapain has the enzymatic sites thereof inactivated with an iodoacetic acid, a salt thereof, an ester thereof derived from an alcohol having from 1 to 6 carbons, or an amide thereof.

5. A microplate having a plurality of microwells, at least one microwell thereof having from 0.01 to 10 micrograms per cm$^2$ of chymopapain adhered to the inner surface thereof; each microwell being opaque to light; and the chymopapain having its enzymatic sites inactivated with full retention of its allergenic properties.

6. The microplate of claim 5 wherein the microwell is made of opaque organic polymer.

7. The microplate of claim 5 wherein the chymopapain has the enzymatic sites thereof inactivated with an iodoacetic acid, a salt thereof, an ester thereof derived from an alcohol having from 1 to 6 carbons, or an amide thereof.

* * * * *